(12) United States Patent
Mennicken et al.

(10) Patent No.: US 9,518,900 B2
(45) Date of Patent: Dec. 13, 2016

(54) SAMPLE PREPARATION SYSTEM FOR AN ANALYTICAL SYSTEM FOR DETERMINING A MEASURED VARIABLE OF A LIQUID SAMPLE

(71) Applicant: Endress + Hauser Conducta Gesellschaft für Mess- und Regeltechnik mbH + Co. KG, Gerlingen (DE)

(72) Inventors: Guido Mennicken, Leonberg (DE); Ralf Steuerwald, Eberdigen (DE); Maike Springmann, Stuttgart (DE); Matthias Knodler, Fellbach (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 860 days.

(21) Appl. No.: 13/709,652

(22) Filed: Dec. 10, 2012

(65) Prior Publication Data

US 2013/0149790 A1    Jun. 13, 2013

(30) Foreign Application Priority Data

Dec. 12, 2011    (DE) .................. 10 2011 088 235

(51) Int. Cl.
| | | |
|---|---|---|
| *G01N 1/34* | (2006.01) | |
| *G01N 1/38* | (2006.01) | |
| *G01N 1/40* | (2006.01) | |

(52) U.S. Cl.
CPC ........ *G01N 1/34* (2013.01); *G01N 1/38* (2013.01); *G01N 2001/4088* (2013.01); *Y10T 436/25125* (2015.01)

(58) Field of Classification Search
CPC .............. G01N 1/34; G01N 1/38; G01N 1/14; G01N 1/10; G01N 2001/4088; Y10T 436/25125

See application file for complete search history.

(56) References Cited

U.S. PATENT DOCUMENTS 3,733,906 A    5/1973   Barnhardt et al.
4,454,773 A *  6/1984   Brunner ............... E21B 49/086
                                                141/236

(Continued)

FOREIGN PATENT DOCUMENTS

| CN | 1811456 A | 8/2006 |
|---|---|---|
| DE | 2 134 935 A1 | 5/1972 |

(Continued)

OTHER PUBLICATIONS

German Search Report in corresponding application 10 2011 088 235.9, dated Jun. 26, 2012.

*Primary Examiner* — Christopher A Hixson
(74) *Attorney, Agent, or Firm* — Christopher R. Powers; PatServe

(57) ABSTRACT

A sample preparation system for an analytical system for determining a measured variable of a sample liquid, comprising: a transport unit connected with a sample taking location via a first fluid conducting line; a sample collecting unit, which serves the analytical system as a staging area for automated removal of liquid samples, based on which the measured variable is determined; a filter unit arranged between the sample taking location and the transport unit; and at least one reservoir connected via a second fluid conducting line with the filter unit for providing a cleaning medium for cleaning the filter unit; wherein the transport unit is embodied to transport sample liquid from the sample taking location through the filter unit into the sample collecting unit. The cleaning medium includes an oxidizing agent.

13 Claims, 1 Drawing Sheet

(56) References Cited

U.S. PATENT DOCUMENTS

| | | | | |
|---|---|---|---|---|
| 5,098,261 | A * | 3/1992 | Bertoncini | ........ A61M 5/14228 |
| | | | | 417/474 |
| 6,550,348 | B1 * | 4/2003 | Wolcott | ................... G01N 1/10 |
| | | | | 73/863.24 |
| 2010/0085568 | A1 * | 4/2010 | Robertson, Jr. | ........... G01J 3/02 |
| | | | | 356/319 |

FOREIGN PATENT DOCUMENTS

| | | |
|---|---|---|
| DE | 24 49 112 A1 | 5/1975 |
| DE | 692 25 940 T2 | 11/1998 |
| DE | 102 22 822 A1 | 12/2003 |
| DE | 60 2005 005 756 T2 | 4/2009 |
| DE | 11 2008 002 979 T5 | 11/2010 |
| DE | 10 2009 029 305 A1 | 3/2011 |
| DE | 10 2010 030 489 A1 | 9/2011 |
| EP | 0669159 A1 * | 2/1995 |
| WO | 02/090937 A2 | 11/2002 |
| WO | 2011/029698 A1 | 3/2011 |

* cited by examiner

SAMPLE PREPARATION SYSTEM FOR AN ANALYTICAL SYSTEM FOR DETERMINING A MEASURED VARIABLE OF A LIQUID SAMPLE

TECHNICAL FIELD

The invention relates to a sample preparation system for an analytical system for determining a measured variable of a liquid sample and to a method for preparing a sample liquid.

BACKGROUND DISCUSSION

In process measurements technology, for example, in chemical, biotechnological, pharmaceutical and food technical processes, and in environmental technology, automatic analytical devices or analyzers are frequently used for determining a measured variable of a liquid sample. For example, analytical devices can be applied for monitoring and optimizing the cleaning effectiveness of a clarification plant, for monitoring drinking water or for quality monitoring of food. Measured and monitored is, for example, the content in the liquid sample of a certain substance, which is also referred to as the analyte. Analytes can be, for example, ions, such as ammonium, phosphate, silicate or nitrate, biological or biochemical compounds, e.g. hormones, or even microorganisms. Other measured variables, which are determined by analytical devices in process measurements technology, especially in the field of monitoring water, include total carbon content (TOC) and chemical oxygen demand (COD). Analytical devices can be embodied, for example, as cabinet devices or as buoys.

Frequently in analytical devices, the sample to be analyzed is treated by mixing with one or more reagents, so that a chemical reaction can occur in the liquid sample. Preferably, the reagents are so selected that the chemical reaction is detectable by means of physical methods, for example, by optical measurements, by means of potentiometric or amperometric sensors or by measuring conductivity. For example, the chemical reaction can bring about a coloring or a color change, which is detectable with optical means. The color intensity is, in this case, a measure for the measured variable to be determined. The measured variable can be ascertained, for example, photometrically, in that electromagnetic radiation, for example, visible light, is radiated from a radiation source into the liquid sample and after transmission through the liquid sample is received by a suitable receiver. The receiver produces a measurement signal dependent on the intensity of the received radiation, from which the measured variable can be derived.

In order to use such analytical methods in an automated fashion, for example, for industrial applications or for monitoring a clarification plant or a body of water in the outdoors, it is desirable to provide an analytical device, which performs the required analytical method in an automated fashion. The most important requirements for such an analytical device are, besides a sufficient accuracy of measurement, robustness, simple serviceability and the assurance of a sufficient working-, and environmental safety.

Semiautomatic and automatic analytical devices are known from the state of the art. Thus, for example, DE 102 22 822 A1, DE 102 20 829 A1 and DE 10 2009 029305 A1 disclose online-analyzers for analyzing samples. These online-analyzers are embodied, in each case, as cabinet devices, which include a control unit, supply containers for reagents, standard solutions and cleaning liquids, pumps for transporting and dosing liquid samples, and the one or more reagents, into measuring cell, and measuring transducers for optical measurements on the liquid sample treated with the one or more reagents in the measuring cell. The reagents, standard solutions or cleaning liquids are transported from the supply containers and into the measuring cell. Used liquid is transferred from the measuring cell into a waste container.

In a large number of applications of such analytical devices, especially in the environmental field, the liquids to be analyzed, or monitored, can have a certain solids fraction, which can be noticed, for example, as turbidity. The solids fraction can, in the case of analytical methods, which include optical measurements as above described, lead to a corruption of the analytical result or even make measuring impossible. For example, a large amount of particles in the liquid can lead to the result that a coloring of the liquid sample is no longer detectable. The liquid is therefore frequently filtered before performing the actual analytical method. From the filtrate then a predetermined sample amount is fed into the processing unit of the analytical device and there treated and analyzed in the above described manner.

From time to time, a cleaning of the filter is required, since the particles contained in the liquid can plug the filter. Additionally, there is, for example, in the case of environmental technology and biotechnological applications, the danger that microorganisms, for example, bacteria, algae or fungi, can be held tightly in the filter and spread on the filter substrate and into its pores and, finally, likewise lessen flow through the filter.

SUMMARY OF THE INVENTION

It is therefore an object of the invention to provide an apparatus and a method, which permit effective cleaning of a filter used for preparing the sample liquid before the performing of an analysis in an automatic analytical device.

This object is achieved by a sample preparation system as defined in claim 1 and a method as defined in claim 12.

This object is achieved by a sample preparation system and a method sample preparation system for an analytical system for determining a measured variable of a sample liquid includes:
- a transport unit connected with a sample taking location via a first fluid conducting line;
- a sample collecting unit, which serves the analytical system as a staging area for automated removal of liquid samples to be analyzed;
- a filter unit arranged between the sample taking location and the transport unit; and
- at least one reservoir connected via a second fluid conducting line with the filter unit for providing a cleaning medium, including an oxidizing agent, for cleaning the filter unit;

wherein the transport unit is embodied to transport sample liquid from the sample taking location through the filter unit into the sample collecting unit.

The application of a cleaning medium including an oxidizing agent for cleaning the filter unit leads not only to an improved cleaning action compared with simple washing of the filter with a usual detergent but also kills microorganisms, such as bacteria, algae and/or fungi, in given cases, inhabiting the filter and so prevents their further spreading.

The sample preparation system can furthermore include a first valve unit, by means of which a first section of the first fluid conducting line extending between the filter unit and the first valve unit can be connected selectively with a second section of the first fluid conducting line extending between the valve unit and the transport unit or with the second fluid conducting line. A valve unit can include one or a number of valves, especially one or a number of multiport valves, or one or more valves with associated control mechanisms. In a first state of the first valve unit, the first section of the first fluid conducting line can be connected with the transport unit via the second section of the first fluid conducting line, so that the transport unit can transport the sample liquid through the filter unit and via the first fluid conducting line into the sample collecting unit. In a second state of the first valve unit, the first section of the first fluid conducting line can be connected via the second fluid conducting line with the reservoir for a cleaning medium, so that cleaning medium can flow into the first section of the first fluid conducting line and then through the filter unit.

The sample preparation system can include a control unit, which is embodied to control the valve unit and the transport unit, as well as, in given cases, a pump associated with the reservoir for a cleaning medium, in such a manner that, in a first operating mode of the sample preparation system, liquid sample is led from the sample taking location into the sample collecting unit, and, in a second operating mode, cleaning medium is led from the reservoir for a cleaning medium into the first section of the first fluid conducting line and through the filter unit.

The second section of the first fluid conducting line can, in an additional embodiment of the sample preparation system, be connected, for example, via a second valve unit, selectively with the sample collecting unit or with an outlet, especially an outlet leading to a waste container. The second valve unit can, like the first valve unit, be composed of one or more valves, e.g. one or more multiport valves, or a centralized unit of one or more valves with associated control mechanisms.

In the above mentioned, first operating mode of the sample preparation system, the second valve unit connects in its first state the second section of the first fluid conducting line with the sample collecting unit. In a third operating mode, the second valve unit connects the second section of the first fluid conducting line with the outlet. In this mode, sample liquid transported via the first fluid conducting line can be discarded. This can be utilized, for example, in order, after a cleaning of the filter unit performed in the second operating mode, to wash out the first fluid conducting line with filtrate. Therewith, it can be assured that no residual cleaning medium still in the first fluid conducting line after the cleaning is transported into the sample collecting unit.

The second fluid conducting line can, in an additional embodiment, likewise be connected selectively with the sample collecting unit or with the outlet. This permits an additional cleaning of the associated lines and/or the sample collecting unit.

The transport unit can be a pump, for example, a membrane pump, a piston pump or a peristaltic pump.

The filter unit can extend, at least sectionally, into liquid present at the sample taking location.

The cleaning medium can be a liquid, a gas or a gas mixture, wherein the liquid, the gas or the gas mixture can comprise ozone as the oxidizing agent. The oxidizing agent can also be chlorine or chlorine containing compounds, such as hypochlorous acid.

The reservoir for a cleaning medium can comprise a containment, in which the cleaning medium is contained, and/or a connection to the transport line of a cleaning medium from an external reservoir not belonging to the sample preparation system, for example, a connection to a compressed air line. The reservoir for a cleaning medium can also comprise an apparatus for producing the oxidizing agent. Ozone is especially advantageous as the oxidizing agent, since it is manufacturable easily on-site by means of an ozone generator. The reservoir for a cleaning medium can, in an embodiment, comprise a number of containers with different cleaning media. For example, a cleaning medium can comprise a liquid detergent or a cleaning gas.

If a liquid is provided as cleaning medium, the reservoir for a cleaning medium can include at least one container containing the liquid cleaning medium and at least one pump embodied to transport the cleaning medium from the container into the second fluid conducting line. If the cleaning medium is a gas, e.g. air or ozone, this can be provided from a compressor or from a container under pressure. Then no additional pump is required for transporting compressed gas into the second fluid conducting line.

In an additional embodiment, the reservoir for a cleaning medium can have a container containing a liquid cleaning medium and, associated with such container, a pump, for example, a membrane pump, embodied for transporting the cleaning medium from the container into the second fluid conducting line, and, supplementally, a connection for a transport line for transporting compressed cleaning gas, for example, air or ozone, into the second fluid conducting line. The reservoir for a cleaning medium includes, in this embodiment, a valve unit, for example, a multiport valve, by means of which the second fluid conducting line can be connected selectively with the container containing the liquid cleaning medium or with the connection for the transport line for compressed cleaning gas.

In the above mentioned, second operating mode of the sample preparation system, the first valve unit connects the first section of the first fluid conducting line with the second fluid conducting line for transporting cleaning medium through the filter unit in the direction of the sample taking location. If the reservoir for a cleaning medium has a container containing a liquid cleaning medium and a pump associated with the container for transporting the liquid cleaning medium from the container into the second fluid conducting line, the pump associated with the container serves in this operating mode for transporting the cleaning medium from the second fluid conducting line via the first valve unit into the first fluid conducting line, through the filter unit and finally into the sample taking location. The filter unit is, in this way, cleaned by means of the cleaning agent flowing through the filter unit.

If the reservoir for a cleaning medium has a connection for a compressed cleaning gas, transport line, for example, for a cleaning gas such as air or ozone, into the second fluid conducting line, in this operating mode, the compressed gas is transported via the second fluid conducting line, the first valve unit and the first section of the first fluid conducting line through the filter unit and into the sample taking location. The gas flowing through the filter unit cleans the filter unit and, if the gas contains an oxidizing agent, such as ozone, also kills microorganisms present in the filter unit.

If the reservoir for a cleaning medium contains a plurality of cleaning media, it suffices for cleaning the filter, including killing microorganisms inhabiting the filter, that at least one of the cleaning media contains an oxidizing agent, e.g. ozone.

The above mentioned control unit can be embodied to control the valve unit, the transport unit and the pump for the operation of the sample preparation system in the first, second and/or third operating modes, and, in given cases, in additional operating modes. The control unit can be an electronic data processing system, which includes, in a data memory, one or more operating programs, which it can execute for controlling the sample preparation system.

The invention relates also to an analytical system for determining a measured variable of a liquid sample, comprising a sample preparation system according to one of the above described embodiments, and further comprising an analyzer comprising:
  a measuring cell;
  at least one liquid container containing a treatment liquid for treating the liquid sample;
  a processing system comprising a transport- and dosing apparatus for transporting and metering the liquid sample from the sample collecting system and the treatment liquid from the liquid container into the measuring cell; and
  a measuring transducer, especially an optical measuring transducer, for providing at least one measurement signal correlated with the measured variable of the liquid sample contained in the measuring cell and treated with the treatment liquid.

The analyzer can supplementally include a control- and evaluating unit, which is embodied to control the analyzer, especially the processing system and the measuring transducer, to perform measurements and to derive from the measurement signal delivered by the measuring transducer a value for the measured variable. The control unit of the analyzer can be embodied to communicate with the control unit of the sample preparation system. Alternatively, the control unit of the analyzer can also undertake the functions of the control unit of the sample preparation system, so that the analytical device, as a whole, has only one control unit. This single control unit can, however, also be embodied in a distributed manner in the form of two or more units communicating with one another.

The method of the invention for preparing a liquid sample for determining a measured variable, especially for determining a concentration of a chemical substance in the liquid sample by means of an automatic analytical system, for example, the above set forth analytical system, includes steps as follows:
  continuous or discontinuous transporting of liquid from a sample taking location through a filter unit into a sample collecting system, from which liquid samples are repeatedly removed for determining the measured variable;
  interrupting the transporting of the liquid;
  washing the filter unit with at least one cleaning medium including an oxidizing agent; and
  continuing the continuous or discontinuous transporting of the liquid from the sample taking location through the filter unit into the sample collecting system.

The cleaning medium can be a gas or gas mixture. For example, compressed air and ozone are options as cleaning media. Advantageously, the compressed gas or gas mixture is introduced via a gas connection into a fluid conducting line connected with the filter unit, in order to wash the filter unit, wherein the gas flows through the filter unit in the direction of the sample taking location to wash the filter unit.

BRIEF DESCRIPTION OF THE DRAWINGS

The invention will now be explained in greater detail based on the examples of embodiments illustrated in the drawing, the figures of which show as follows.

DETAILED DISCUSSION IN CONJUNCTION WITH THE DRAWINGS

Figure 1:
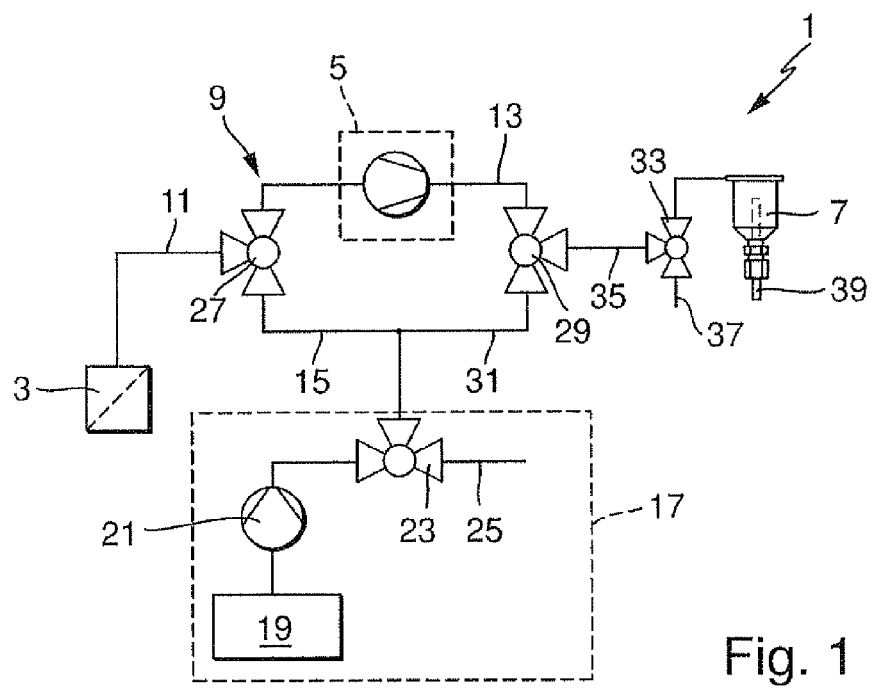
FIG. 1 is a schematic representation of a sample preparation system.

FIG. 1 shows a sample preparation system 1 for an automatic analytical system. Sample preparation system 1 includes a filter unit 3, which during operation of the sample preparation system 1 extends at least sectionally into a liquid to be sampled present at a sample taking location. The filter unit is connected via a first fluid conducting line 9 to a sample collecting unit 7, from which an automatic analytical device (FIG. 2) can withdraw via the connection 39 liquid samples for determining a measured variable of the sample liquid, for example, the concentration of one or more analytes. Sample preparation system 1 includes a transport unit embodied in the example shown here in the form of a peristaltic pump 5, which serves to transport sample liquid from the sample taking location through the filter unit 3 and via the first fluid conducting line 9 into the sample collecting unit 7.

The first fluid conducting line 9 includes a first section 11, which connects the filter unit 3 with a first valve unit 27. Valve system 27, in a first state, connects the first section 11 of the first fluid conducting line 9 with a second section 13 of the first fluid conducting line 9. In the example shown here, the second section 13 corresponds to the hose of the peristaltic pump 5. The hose of the peristaltic pump can be connected with the valve units 27 and 29 via intermediate pieces, e.g., in each case, via a piece of Teflon tube. In a second state, the first valve unit 27 connects the first section 11 of the first fluid conducting line 9 with a second fluid conducting line 15, which is connected with a reservoir 17 for a cleaning medium. The first valve unit 27 is embodied in such a manner that, in the first state, a transporting of the liquid sample into the second fluid conducting line is suppressed, while in the second state no flow of cleaning medium from the second fluid conducting line into the second section 13 of the first fluid conducting line 9 is possible. To accomplish this, valve unit 27 can be embodied, for example, as a 3/2 valve.

The reservoir 17 for a cleaning medium includes a liquid container 19, in which a liquid cleaning medium, for example, water or a detergent, is contained, as well as a gas connection 25, via which compressed cleaning gas or a gas mixture, for example, compressed air, ozone, oxygen or ozone containing, compressed air, can be introduced into the second fluid conducting line 15. Associated with the liquid container 19 is a pump, here a membrane pump 21, which serves to transport the liquid cleaning medium contained in the liquid container 19 into the second fluid conducting line 15. The liquid container 19 and its associated membrane pump 21 and the gas connection 25 are connected with the second fluid conducting line 15 via a second valve unit 23. Valve unit 23 is embodied in the example shown here as a 3/2 valve. In a first state of the second valve unit 23, the second fluid conducting line 15 is connected with the liquid container 19, while in a second state of the second valve unit 23, the second fluid conducting line 15 is connected with the gas connection 25, so that, selectively, the liquid cleaning medium or a cleaning gas can be transported into the second fluid conducting line.

The second fluid conducting line 15 is connected at a junction with a third fluid conducting line 31, which, in turn, can be connected via a third valve unit 29 with a third section 35 of the first fluid conducting line 9. The third valve unit 29 is likewise connected with the second section 13 of the first fluid conducting line 9, so that the third section 35 of the first fluid conducting line 9 can be connected selectively either with the third fluid conducting line 31 or the second section 13 of the first fluid conducting line 9. Valve unit 29 is embodied in the example shown here as a 3/2 valve. The third section 35 of the fluid conducting line 9 is connectable via a fourth valve unit 33 selectively either with the sample collecting unit 7 or with a liquid discharge 37.

In a first operating mode, the sample preparation system 1 transports sample liquid from the sample taking location into the sample collecting unit 7. In this operating mode, the first valve unit 27 is brought into its first valve state, in which the first section 11 of the first fluid conducting line 9 is connected with the second section 13 of the fluid conducting line 9, while flow through the first section 11 of the fluid conducting line 9 into the second fluid conducting line 15 is blocked. At the same time, in this operating mode, the third valve unit 29 is located in a state, in which the second section 13 of the first fluid conducting line 9 is connected with the third section 35 and a flow of liquid from the second section 13 of the first fluid conducting line 9 into the third fluid conducting line 31 is suppressed. The fourth valve unit 33, which in the example shown here is embodied as 3/2 valve, simultaneously connects the third section 35 with the sample collecting unit 7. In this operating mode, peristaltic pump 5 transports sample liquid from the sample taking location through the filter unit 3 and the first fluid conducting line 9 into the sample collecting unit 7.

From time to time, the first operating mode is interrupted, in order to clean the filter unit 3. For this, the sample preparation system is operated in a second operating mode. In such case, the first valve unit 27 is brought into a second state, in which the first section 11 of the first fluid conducting line 9 is connected with the second fluid conducting line 15, while flow of liquid from the first section 11 or from the second fluid conducting line 15 into the second section 13 of the first fluid conducting line 9 is suppressed. The third valve unit 29 in this operating mode also blocks the second fluid conducting line 15 from the second section 13 and the third section 35 of the first fluid conducting line 9. In this operating mode, thus the reservoir 17 for a cleaning medium is connected with the first section 11 of the first fluid conducting line 9 and the filter unit 3. Optionally in this operating mode, the filter unit 3 can be washed with the cleaning liquid contained in the container 19 and/or with a cleaning gas fed-in via the gas connection 25. In such case, it is assured that no cleaning medium gets into the second section 13 of the first fluid conducting line 9 and therewith into the peristaltic pump 5.

The sample preparation system 1 shown in FIG. 1 also permits the filter unit 3 to be washed sequentially, first with the cleaning gas, e.g. ozone and/or compressed air, and then with the cleaning liquid. For this, the second valve unit 23 can be brought, first of all, into its first state, in which the gas connection 25 is connected via the second fluid conducting line 15 and the first section 11 of the first fluid conducting line 9 with the filter 3, while the liquid container 19 and the associated membrane pump 21 of the second fluid conducting line 15 are blocked.

Options for the cleaning gas include compressed air, which, when it is led through the filter unit 3 and effects a purely mechanical removal of dirt particles inhabiting the filter pores. In order to kill microorganisms in the filter unit 3 and also to achieve a generally improved cleaning effectiveness, the cleaning gas can, supplementally or alternatively to the compressed air, contain an oxidizing agent. For example, a gas mixture of compressed air and ozone, or pure ozone, can be used as cleaning gas.

Ozone can be provided, for example, on-site by an ozone generator connected with the gas connection 25. During passage through the filter unit 3, the ozone acts in an oxidizing manner on all organic residues in the filter. Clinging microorganisms are reliably killed and, for the large part, removed with the gas flow through the filter. It is also possible to wash the filter unit first with ozone and then with compressed air.

Then, for improving the cleaning result, the second valve unit 23 can be brought into its second state, in which the liquid container 19 is connected with the second fluid conducting line 15 and the filter unit 3, while a flow of cleaning gas into the fluid conducting line 15 is blocked by the valve unit 23. In this state of the valve unit 23, the membrane pump can transport cleaning liquid in the direction of the sample taking location back through the filter unit 3. In this way, those particles are removed from the filter unit, which were still not completely oxidized to a gaseous reaction product by means of the ozone earlier conducted through the filter unit 3 or still not completely removed mechanically by the gas stream.

The liquid cleaning medium can be, for example, water, a detergent or an aqueous cleaning solution containing an oxidizing agent, especially dissolved ozone.

In order to remove residual cleaning liquid in the first section 11 of the first fluid conducting line 9 and in the filter unit 3 before resuming transport of sample liquid in the first operating mode of the sample preparation system 1, a further washing step can be performed with the cleaning gas. For this, the valve unit 23 is brought anew into its first state, in which the gas connection 25 is connected via the valve unit 23 with the second fluid conducting line 15, while a flow of cleaning liquid from the liquid container 19 into the second fluid conducting line 15 is suppressed. In this state of the valve unit 23, in the case of retained state of the valve unit 27, the compressed cleaning gas is transported into the first section 11 of the first fluid conducting line 9 and in the direction of the sample transport through the filter unit 3. In this way, the fluid conducting line 9 and the filter unit 3 are "blown free" of cleaning liquid.

Of course, it is also possible, instead of the here described method with three cleaning steps, which comprise, first of all, the washing with cleaning gas, then the washing with cleaning liquid and, finally, the renewed washing with cleaning gas, to wash the filter unit 3, first of all, with the liquid cleaning medium and then with the cleaning gas. Also options are method variants, in which either the liquid cleaning medium or the cleaning gas or both comprise an oxidizing agent.

By means of the valve units 27 and 29 blocking the second section 13 of the first fluid conducting line 9 during the cleaning from the second fluid conducting line 15, it is prevented that cleaning medium containing oxidizing agent can get into the peristaltic pump 5. This is especially advantageous for the application of peristaltic pumps, whose hose in contact with the oxidizing agent can experience aging phenomena, such as e.g. a lessening of its elasticity.

It is also possible with the sample preparation system 1 illustrated in FIG. 1, instead of washing the filter unit with the cleaning liquid contained in the liquid container 19, to back wash the filter unit 3 with filtrate. In this case, the second valve unit 23 is brought into a state, in which the reservoir 19 for a cleaning medium is blocked from the second fluid conducting line 15. For back transport of the filtrate through the liquid line 9, the peristaltic pump 5 can be operated in direction opposite to that used for transporting sample liquid into the sample collecting unit 7. It is advantageous, after washing the filter system with a cleaning medium and before the new conveying of sample liquid from the sample taking location into the sample collecting unit 7, first, to back wash the filter unit 3 briefly in the described manner with filtrate, in order to refill the first section 11 of the fluid conducting line 9 with filtrate. In this way, it is prevented that residual cleaning medium in the first section 11, upon restarting the first operating mode of the sample preparation system 1 for transporting sample liquid from the sample taking location, gets into the sample collecting unit 7 and therewith into the analytical device.

Alternatively or supplementally, an option is, directly after washing the filter unit 3 with cleaning medium, to resume transporting sample liquid via the first fluid conducting line 9, while, however, not transporting the sample liquid immediately into the sample collecting unit 7, but, instead, discarding the supplied sample liquid for a certain time span via the liquid discharge 37. To this end, the fourth valve unit 33 is so set that the liquid line 9 is not connected with the sample collecting unit 7, but, instead, with the outlet 37.

Even when, after washing the filter unit 3 with cleaning medium, the first section 11 of the first fluid conducting line 9 and the filter unit 3 have been freed of residues of cleaning medium by rewashing with cleaning gas and/or filtrate, so that the line section 11 and the filter unit 3 thus then only contained air, or cleaning gas, it is still advantageous, upon resuming transporting sample liquid via the first fluid conducting line 9, not to transport the supplied sample liquid immediately into the sample collecting unit 7, but, instead, for a certain time span, to discard the supplied sample liquid via the liquid discharge 37. In this way, a defined state of the filter unit 3 and the fluid conducting line 9 up to the fourth valve unit 33 is assured. Also, in the case of first start-up of the apparatus or in the case of renewed start-up after a longer period of time, in which the apparatus was not in operation, it is sensible, first of all, for a certain time span to transport sample liquid through the filter unit 3 and via the fluid conducting line 9 and to discard such via the liquid discharge 37. After expiration of the predetermined time span, then the fluid conducting line 9 is connected with the sample collecting unit 7 by means of the valve unit 33, in order then to transport the sample liquid into the sample collecting unit 7.

Figure 2:
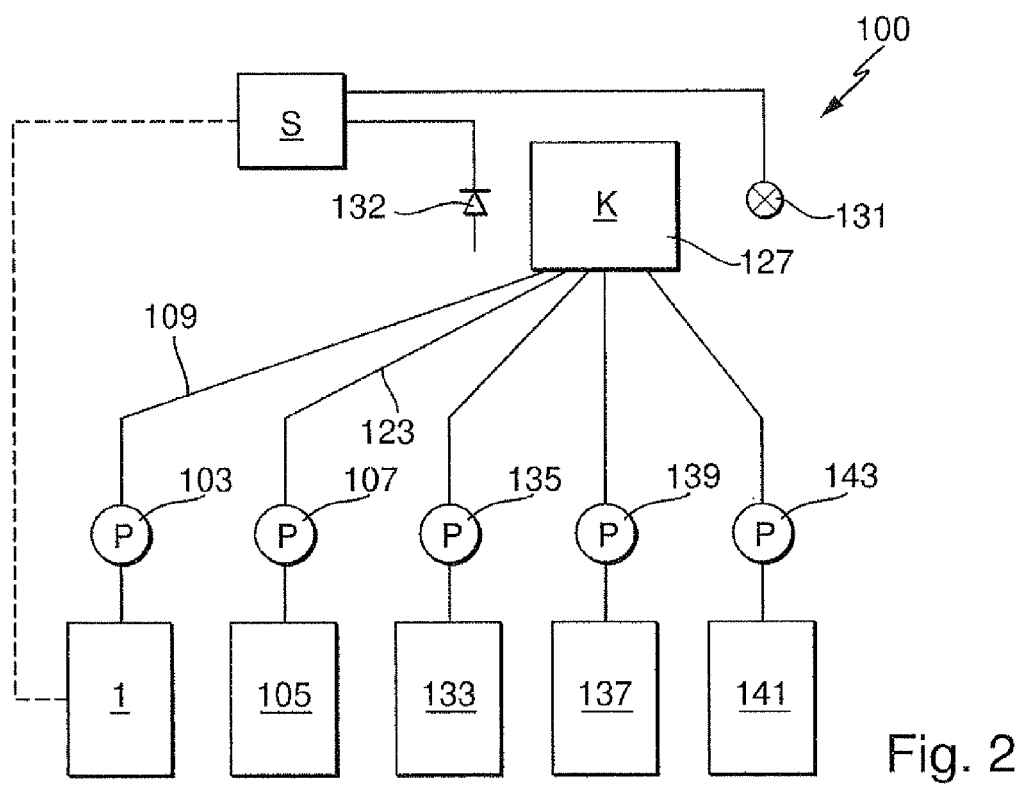
FIG. 2 is a schematic representation of an automatic analytical system with an analyzer in the form of an analytical device and with a sample preparation system.

FIG. 2 shows schematically an analytical system with an analyzer in the form of an analytical device 100 for determining a measured variable of a liquid sample. The analytical device 100 includes a plurality of supply containers 133, 137 and 141, a processing system with a plurality of pumps 135, 139 and 143 for transporting and metering liquids contained in the supply containers 133, 137 and 141, and liquid lines, via which the supply containers 133, 137, 141 are connected with measuring cell 127. Additionally, the analytical device 100 has a waste container 105, which is likewise connected with the measuring cell 127 via a pump 107. The pumps 107, 135, 139 and 143 can be, for example, membrane pumps, piston pumps, especially syringe pumps, or peristaltic pumps. Furthermore, the analytical system includes the sample preparation system 1 shown in FIG. 1, especially the sample collecting unit 7, in which the filtered sample liquid is contained. The sample collecting unit 7 serves the analytical device 100 as sample supply, from which a liquid sample of predetermined volume is removed for performing an analysis. The sample collecting unit 7 is connected with the measuring cell 127 via the transport line 109. Serving for conveying and dosing the liquid sample into the measuring cell 127 is pump 103, which, like the remaining pumps 107, 135, 139, 143, can be embodied, for example, as a membrane pump, a piston pump, especially a syringe pump, or a peristaltic pump.

For registering the measured variable to be determined by the analytical device 100, the analytical device 100 includes an optical measuring transducer, which includes radiation source 131 and a receiver 132, which are so arranged relative to the measuring radiation transparent measuring cell 127 that the measuring radiation passes from the source 131 through a liquid sample contained in the measuring cell 127 and then strikes the receiver 132.

The analytical device 100 can be operated in a completely automated fashion. For this, it possesses a control unit S, which in the example shown here also performs the functions of an evaluating unit, especially the determining of a measured variable based on a measured value registered by the measuring transducer. In the example shown here, the control unit S serves, moreover, for controlling the sample preparation system 1 in the manner described based on FIG. 1. It is, however, also possible that the sample preparation system 1 has its own control system, which can be embodied for communication with the control system S of the analytical device. Control unit S includes a data processing system and a memory, in which one or more operating programs are stored, which serve for control of the analytical device 100 and/or control of the sample preparation system 1, as well as, in given cases, evaluation of the measurement signals delivered by the optical measuring transducer 131, 132. The data processing system can also include an input apparatus for input of commands or parameters by a service person and/or an interface for the receipt of commands, parameters or other data from a superordinated unit, for example, from a process control system. Additionally, the control unit S can also include an output apparatus for output of data, especially measurement results, or operating information, to a user or even include an interface for output of data to the superordinated unit. The control unit S is connected with drives of the pumps 103, 107 135, 139, 143 and with valves (not shown), in order to operate such for transporting liquids from the sample collecting unit and the supply containers 133, 137 and 141 into the measuring cell 127 in an automated fashion. The control unit S is, moreover, connected with the measuring transducer, in order to control such and to ascertain the measured variable from measurement signals of the receiver 132.

The supply container 141 can contain a reagent, @which is mixed with the sample removed from the sample collecting unit 7 for treating such sample. If the measured variable to be determined is, for example, the concentration of an analyte in the liquid, the reagent can be so selected that it reacts with the analyte to form a colored reaction product. The intensity of the color is then a measure for the concentration to be determined. The wavelength of the measuring radiation transmitted by the radiation source 131 is, in this case, matched to the color of the reaction product and is correspondingly evaluated by the receiver 132, respectively the control unit S. Instead of a single reagent as in the example shown here, depending on measured variable to be determined, also a plurality of reagents can be applied. In this case, the analytical device 100 has a corresponding number of supply containers for the required reagents.

In measurement operation of the analytical device 100, the control unit S first doses a predetermined amount of the sample liquid contained in the sample collecting unit 7 into the measuring cell 127 as liquid sample to be analyzed. At the same time, or there upon, the control unit S controls the pump 143, in order to transport a predetermined amount of the reagent contained in the supply container 141 into the measuring cell. Measuring cell 127 serves thus in the here described example also as mixing cell, in which the liquid sample and reagent are mixed with one another. There are, however, also other embodiments possible, in which the reagent or a plurality of reagents for treating the liquid sample are mixed with one another before the liquid sample treated by means of the reagents is metered into the measuring cell 127.

For registering the measured variable to be determined for the treated liquid sample contained in the measuring cell, the control unit S operates the measuring transducer 131, 132 and evaluates the measurement signal output by the measuring transducer 131, 132. The measured variable ascertained from the measurement signal by the control unit S can be stored in a data memory of the control unit, and/or output via an interface to a superordinated unit and/or via a display of the control unit S.

After determining the measured variable, the measuring cell 127 is emptied by transporting the used liquid sample contained in the measuring cell by means of the pump 107 into the waste container 105. The analytical device 100 has other supply container 133, 137, which can contain standard solutions for calibrations and/or cleaning solutions for cleaning. By means of the pumps 135, 139 associated with supply containers 133, 137, their solutions can be transported into the measuring cell 127.

After one or more completed measuring cycles, a calibrating of the analytical device can be performed by transporting a calibration standard from the supply container 137 into the measuring cell 127. The calibration standard is treated, like a "real" liquid sample from the sample supply, in the measuring cell 127 with reagent transported by means of pump 143 from the supply container 141 into the measuring cell 127. By means of the measuring transducer 131, 132, a measured value of the measured variable is photometrically determined and, in given cases, based on the measured value known for the calibration standard, an adjusting of the analytical device 100 is performed.

The invention claimed is:

1. A sample preparation system for an analytical system for determining a measured variable of a sample liquid, comprising:
    a first fluid conducting line;
    a second fluid conducting line;
    a transport unit with a pump connected with a sample taking location via said first fluid conducting line;
    a sample collecting unit with a container, which serves the analytical system as a staging area for automated removal of liquid samples, based on which the measured variable is determined;
    a filter unit arranged between said sample taking location and said transport unit, the filter unit fluidly connected to the sample collecting unit via the first fluid conducting line; and
    at least one reservoir connected via said second fluid conducting line with said filter unit for providing a cleaning medium for cleaning said filter unit, the second fluid conducting line configured to bypass the transport unit, wherein said transport unit is embodied to transport sample liquid from said sample taking location through said filter unit via said first fluid conducting line into said sample collecting unit and wherein the cleaning medium comprises an oxidizing agent.

2. The sample preparation system as claimed in claim 1, further comprising:
    a first valve unit structured to include a first state and a second state, wherein in the first state, the first valve unit connects a first section of said first fluid conducting line extending between said filter unit and said first valve unit with a second section of said first fluid conducting line extending between said valve unit and said transport unit, while the first valve unit blocks flow through the first section of the first fluid conducting line into the second fluid conducting line, and
    wherein in the second state, the first valve unit connects the first section of said first fluid conducting line with said second fluid conducting line, while the first valve unit blocks flow through the first section of the first conducting line into the second section of the first fluid conducting line.

3. The sample preparation system as claimed in claim 2, further comprising:
    a second valve unit structured to include a first state and a second state of the second valve unit, wherein in the first state, the second valve unit connects said second section of said first fluid conducting line with said sample collecting unit, and in the second state, the second valve unit connects the second section of said first fluid conducting line with an outlet leading to a waste container.

4. The sample preparation system as claimed in claim 1, wherein:
    said filter unit extends, at least partially, into liquid present at the sample taking location.

5. The sample preparation system as claimed in claim 1, wherein:
    the cleaning medium comprises a liquid, a gas or a gas mixture
    comprising ozone as the oxidizing agent.

6. The sample preparation system as claimed in claim 1, wherein the at least one reservoir for a cleaning medium comprises an apparatus for producing the oxidizing agent.

7. The sample preparation system as claimed in claim 1, wherein said transport unit is a peristaltic pump.

8. The sample preparation system as claimed in claim 6, wherein:
    said reservoir for providing a cleaning medium includes a container containing a liquid cleaning agent and a pump, which is embodied to transport the cleaning medium from container into said second fluid conducting line.

9. The sample preparation system as claimed in claim 2, wherein:
    in a first operating mode of the sample preparation system, said first valve unit connects said first section of said first fluid conducting line with said second section of said first fluid conducting line; and
    said second section of said first fluid conducting line is connected with said sample collecting unit via the transport unit for transporting sample liquid from said sample taking location via said filter unit into said sample collecting system.

10. The sample preparation system as claimed in claim 2, wherein in a second operating mode of the sample preparation system, said first valve unit connects said first section of said first fluid conducting line with said second fluid conducting line for transporting cleaning medium through said filter unit in the direction of the sample taking location.

11. An analytical system for determining a measured variable of a liquid sample, comprising:
a sample preparation system, comprising: a first fluid conducting line; second fluid conducting line; a transport unit with a pump connected with a sample taking location via said first fluid conducting line; a sample collecting unit with a container, which serves the analytical system as a staging area for automated removal of liquid samples, based on which the measured variable is determined; an analyzer; a filter unit arranged between said sample taking location and said transport unit, the filter unit fluidly connected to the sample collecting unit via the first fluid conducting line, and at least one reservoir connected via said second fluid conducting line with said filter unit for providing a cleaning medium for cleaning said filter unit the second fluid conducting line configured to bypass the transport unit, wherein: said transport unit is embodied to transport sample liquid from said sample taking location through said filter unit via said first fluid conducting line into said sample collecting unit; and the cleaning medium comprises an oxidizing agent; and
an analytic device, comprising:
a measuring cell;
at least one liquid container containing a treatment liquid for treating the liquid sample;
a processing system comprising a transport- and dosing apparatus for transporting and metering the liquid sample from the sample collecting system and the treatment liquid from the liquid container into the measuring cell; and
an optical measuring transducer for providing at least one measurement signal correlated with the measured variable of the liquid sample contained in the measuring cell and treated with the treatment liquid.

12. The sample preparation system as claimed in claim 6, wherein the apparatus for producing the oxidizing agent is an ozone generator.

13. The analytical system as claimed in claim 11, wherein the measuring transducer is an optical measuring transducer.

* * * * *